(12) United States Patent
Ash

(10) Patent No.: US 11,077,239 B2
(45) Date of Patent: Aug. 3, 2021

(54) TRIBUTARY ACCESS DEVICE AND METHODS OF USE

(71) Applicant: HEMOCLEANSE, INC., Lafayette, IN (US)

(72) Inventor: Stephen Richard Ash, Lafayette, IN (US)

( * ) Notice: Subject to any disclaimer, the term of this patent is extended or adjusted under 35 U.S.C. 154(b) by 614 days.

(21) Appl. No.: 15/916,299

(22) Filed: Mar. 9, 2018

(65) Prior Publication Data

US 2018/0264188 A1 Sep. 20, 2018

Related U.S. Application Data

(60) Provisional application No. 62/473,375, filed on Mar. 18, 2017.

(51) Int. Cl.
| | |
|---|---|
| *A61M 1/36* | (2006.01) |
| *A61B 17/11* | (2006.01) |
| *A61F 2/82* | (2013.01) |
| *A61F 2/24* | (2006.01) |
| *A61F 2/06* | (2013.01) |
| *A61F 2/07* | (2013.01) |

(52) U.S. Cl.
CPC ........... *A61M 1/3653* (2013.01); *A61B 17/11* (2013.01); *A61F 2/82* (2013.01); *A61M 1/3655* (2013.01); *A61M 1/3659* (2014.02); *A61B 2017/1107* (2013.01); *A61B 2017/1135* (2013.01); *A61F 2/06* (2013.01); *A61F 2/064* (2013.01); *A61F 2/07* (2013.01); *A61F 2/2475* (2013.01)

(58) Field of Classification Search
CPC .............. A61M 1/3653; A61M 1/3659; A61M 1/3655; A61F 2/82; A61F 2/2475; A61F 2/064; A61F 2/07; A61F 2/06; A61B 17/11; A61B 2017/1135; A61B 2017/1107
See application file for complete search history.

(56) References Cited

U.S. PATENT DOCUMENTS

| | | | |
|---|---|---|---|
| 4,549,879 A | 10/1985 | Groshong et al. | |
| 5,290,263 A | 3/1994 | Wigness et al. | |
| 2001/0014794 A1* | 8/2001 | Moll ................ | A61B 17/11 604/289 |

(Continued)

FOREIGN PATENT DOCUMENTS

| | | |
|---|---|---|
| RU | 2514536 C1 | 4/2014 |
| RU | 2556787 C2 | 7/2015 |

OTHER PUBLICATIONS

Kapala, A., et al., "Vascular access for chronic dialysis using the superficial femoral vein." The journal of vascular access 4.4 (2003): 150-153.

(Continued)

*Primary Examiner* — Tatyana Zalukaeva
*Assistant Examiner* — Jessica R Arble
(74) *Attorney, Agent, or Firm* — Gutwein Law; Greg N. Geiser

(57) ABSTRACT

Described herein are devices and methods for vascular access via the tributaries. A single lumen catheter, with a bidirectional valve at the tip is disclosed. Flow is out the longitudinal tip of the catheter and not the sides. The two-way valve will act passively but has low opening and closing pressures. A method utilizing endo-to-side port placement of said catheter in vasculature is disclosed. Anastomosis methods are described using said catheter.

14 Claims, 10 Drawing Sheets

(56) References Cited

U.S. PATENT DOCUMENTS

| | | | |
|---|---|---|---|
| 2004/0019315 A1* | 1/2004 | Blatter | A61M 25/10 604/6.16 |
| 2005/0043703 A1* | 2/2005 | Nordgren | A61M 25/0075 604/500 |
| 2009/0018526 A1* | 1/2009 | Power | A61M 25/01 604/508 |

OTHER PUBLICATIONS

Hobbs, John T., et al., "Femoral artery flow, limb blood volume and cardiac output through continuously recorded indicator-dilution curves." Annals of surgery 158.2 (1963): 159.

Radegran, G., et al., "Human femoral artery diameter in relation to knee extensor muscle mass, peak blood flow, and oxygen uptake." American Journal of Physiology-Heart and Circulatory Physiology 278.1 (2000): H162-H167.

Fronek, Arnost, et al., "Common femoral vein dimensions and hemodynamics including Valsalva response as a function of sex, age, and ethnicity in a population study." Journal of vascular surgery 33.5 (2001): 1050-1056.

Ebner, et al., "Minimally Invasive Sutureless Anastomosis of an AV Hemodialysis Graft.", Insert to Endovascular Today Nov. 2014, pp. 98-101.

Maki, Dennis G., et al. "A novel antimicrobial and antithrombotic lock solution for hemodialysis catheters: a multi-center, controlled, randomized trial." Critical care medicine 39.4 (2011): 613-620.

Sauer, Karin, et al., "Effect of a solution containing citrate/Methylene Blue/parabens on Staphylococcus aureus bacteria and biofilm, and comparison with various heparin solutions." Journal of antimicrobial chemotherapy 63.5 (2009): 937-945.

Joh, Jin Hyun, and Ho-Chul Park. "The cutoff value of saphenous vein diameter to predict reflux." Journal of the Korean Surgical Society 85.4 (2013): 169-174.

Beathard, Gerald. History of Vascular Access in Vascular Access Curriculum of ASDIN, Beathard GL Editor, Lippincott, 2006.

Foley, Robert N., and Allan J. Collins. "The USRDS: what you need to know about what it can and can't tell us about ESRD." Clinical Journal of the American Society of Nephrology 8.5 (2013): 845-851.

Nikam, Milind, et al. "Prospective controlled pilot study of arteriovenous fistula placement using the novel Optiflow device." Journal of vascular surgery 61.4 (2015): 1020-1025.

"ESRD: Chapter Two Clinical indicators & preventive care", United States Renal Data System 2013 Annual Data Report, 23 pages.

Ebner, Adrian, et al. "Transcatheter anastomosis connector system for vascular access graft placement: results from a first-in-human pilot study." The journal of vascular access 17.2 (2016): 111-117.

Yevzlin AS; Setum CM; Kallok MJ; Valliant A. Percutaneous AVG Creation in a Canine Model. ASDIN abstract and presentation, 2013 meeting, Feb. 2013.

Adrian Ebner, MD; John Ross, MD; Cindy Setum, PhD; Michael Kallok, PhD; Alexander Yevzlin, MD.Transcatheter Anastomosis Connector System for Vascular Access Graft Placement: Preliminary Results from a First-in-Human Study, ASDIN abstract, 2015 meeting, Feb. 2015.

Sabry AA, Elshafey EM, Alsaran K, Shalaby M, Alsherbeiny S, Abdelkader M. The level of C-reactive protein in chronic hemodialysis patients: A comparative study between patients with noninfected catheters and arteriovenous fistula in two large Gulf hemodialysis centers. Hemodial Int. Jan. 27, 2014.

* cited by examiner

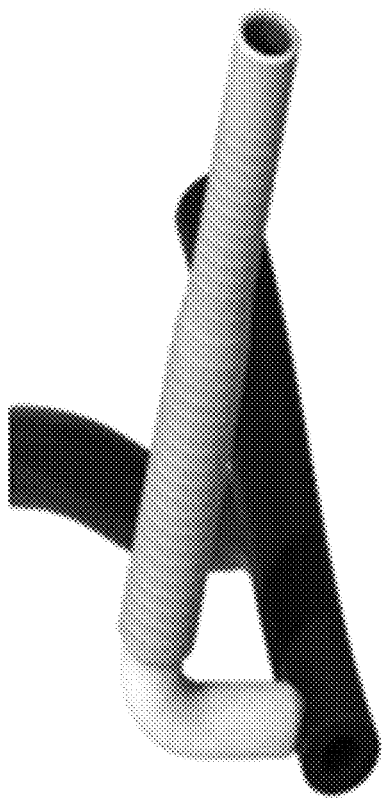
Figure 4A1
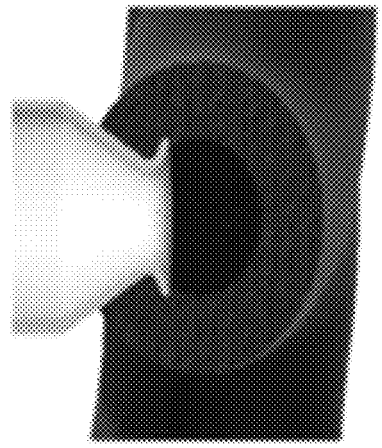
Figure 4A2

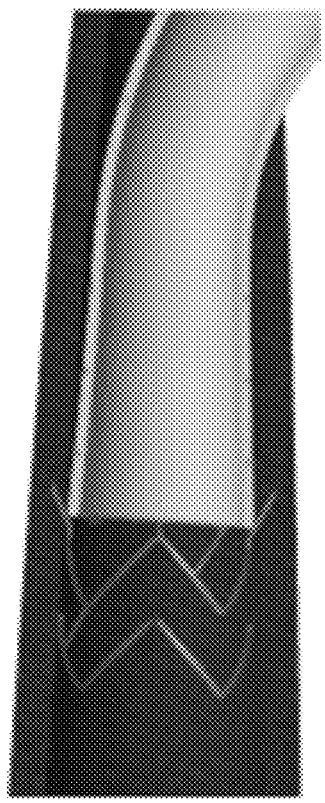
Figure 4A3
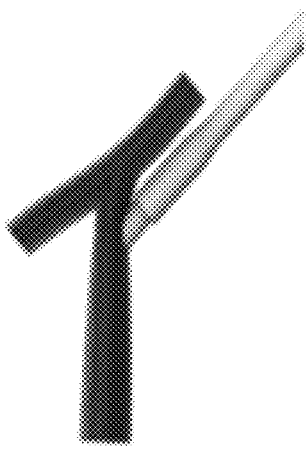
Figure 4A4

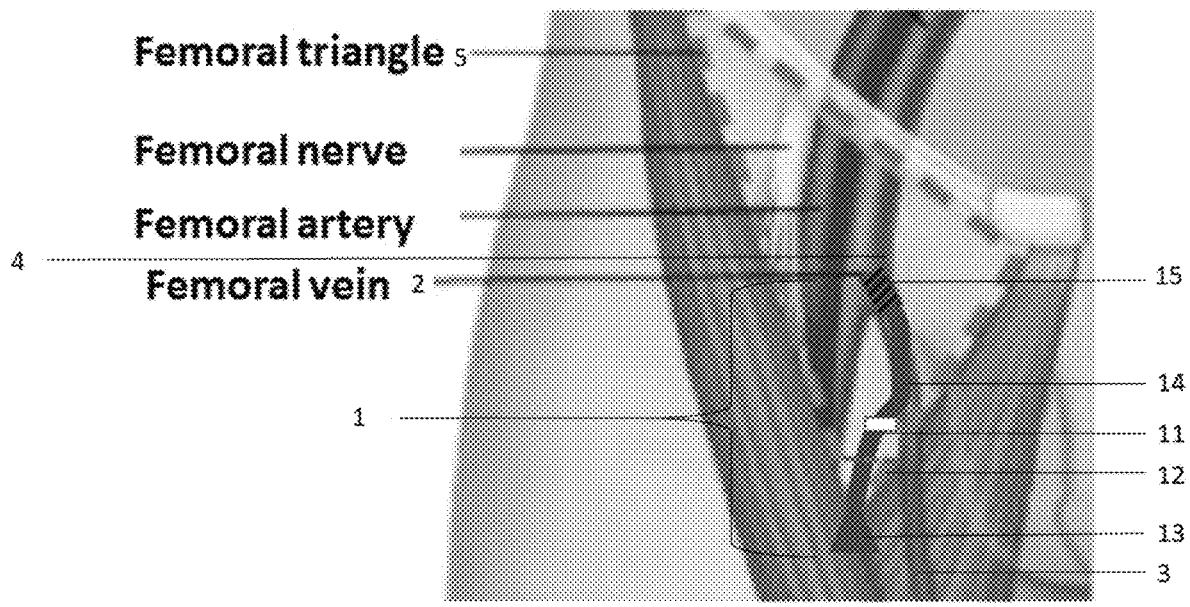

TRIBUTARY ACCESS DEVICE AND METHODS OF USE

CROSS-REFERENCE TO RELATED APPLICATIONS

This application claims the benefit of U.S. provisional patent application Ser. No. 62/473,375, filed on Mar. 18, 2017, which is hereby incorporated by reference.

FIELD

Described herein is a device for vascular access and methods of use.

BACKGROUND

Among the requirements for performing adequate hemodialysis, providing sufficient blood access is the most frustrating, difficult, and expensive. As stated by Dr. Gerald Beathard, "Vascular access is the sine qua non of hemodialysis. Unfortunately, it is also the Achilles' heel." (1)

Three options for chronic blood access were developed between 1960 and 1990: AV fistula, AV graft, and the tunneled and cuffed central venous catheter for dialysis (CVCD). Unfortunately, all three options suffer from complications of stenosis, thrombosis, infection and systemic inflammation. Fistulas and grafts require needle stick insertions to access blood for each dialysis therapy resulting in pain, risk of needle dislodgement and bleeding on needle removal. CVCDs uniformly develop fibrous sheathing wherever they contact the venous wall. When the sheath reaches the tip, it diminishes outflow blood flow rate and often obstructs the catheter completely.

The usual approach for repeated infusion of fluid into veins or removal of blood from veins is to place a cylindrical catheter through the skin and into the vein. A fairly long segment of the catheter lies within the vein, to assure that the tip of the catheter does not exit from the vein if the extremity is moved or if there is tension on the catheter. For example, central venous catheters (CVC) are placed into veins outside the chest or abdomen, and advanced into central veins such as the vena cava. Although these types of catheters are generally successful for at least a few days, there is a significant venous reaction. Histologic studies have shown that if the tip of a very soft catheter merely touches the vein surface, the endothelial cells are completely detached and the surface is denuded. The ensuing inflammatory response forms a neo-intimal structure that soon surrounds the catheter, creating a sheath which eventually becomes fibrous. The sheathing of catheters begins within days after placement of the CVC. The sheath can initiate clotting on its surface and within the vein. When the sheath reaches the tip of the catheter, then withdrawing blood from the catheter is difficult or impossible. Large CVC for dialysis typically lose their ability to withdraw blood over time. Within 60 days of placement about 20-40 percent of such catheters do not provide adequate blood flow rate for dialysis (such as 300 ml/min). Smaller CVC used for fluid infusion and blood sampling fail to deliver adequate blood for analysis, often in the first few days of use. There are no effective therapies for loss of blood outflow from catheters which occurs from sheathing, although thrombolytic drugs such as tissue plasminogen activator can improve flow by removing clots that occur within the sheath or at its tip.

Another consequence of irritation of the vein wall by catheters is stenosis. The inflammatory response of the vein wall occurs at every point of contact with the catheter. This hyperplasia can continue to cause the intima to grow, resulting in stenosis of the vein, or in some cases complete occlusion of the vein. The stenosis and occlusion occur most frequently near the tip of the catheter, where back-and-forth motion of the tip occurs due to body motion, and kinetic energy of flowing blood or fluid impinges on the vein wall. Central venous stenosis may be without symptoms until blood flow rate across the stenosis is increased (such as by creation of a fistula or graft in the extremity draining towards the stenosis). Complete occlusion of a central vein usually leads to physical signs of obstruction, and sometimes to serious symptoms of venous hypertension.

Between uses, CVC are usually filled with anticoagulant solutions such as heparin, injected at the same volume as the internal catheter volume. However, the heparin near the tip does not reach the same concentration as in the upper parts of the catheter, because of the parabolic flow pattern within the catheter. If the catheter has side-holes near the tip, the heparin lock solution is washed out of this part off the catheter almost immediately, due to flow of blood through the side-holes and out the tip. Clotting within the CVC can then occur, which requires forceful fluid injection to remove the clot and sometimes tissue plasminogen activator to dissolve the clot.

The annual cost for maintaining a patient with End Stage Renal Disease (ESRD) on hemodialysis is about $87,000 per year (2). Of this approximately 25% is spent on vascular access placement and maintenance. The 2014 NIH Omnibus solicitation requested a "means to improve physiologic homeostasis in maintenance dialysis therapy through the: improvement of blood access to permit continuous access to the circulation with minimal inflammation." A totally venous vascular access device allowing reliable removal and return of 250 to 400 mL/min blood flow without complications would be a benefit to patients with ESRD. Such an access would be well suited for intermittent outpatient hemodialysis (perhaps with slightly longer treatment time, which is actually beneficial), nighttime dialysis, and new options for treatment such as the wearable artificial kidney or nocturnal dialysis.

U.S. Pat. No. 5,290,263 A discloses a single lumen catheter with a bidirectional check valve assembly that permits flow out of the sides of the catheter. U.S. Pat. No. 4,549,879 A discloses a single lumen catheter with a two-way valve consisting of a slit in the side of the catheter tip. The valve in the '879 is described as a linear slit extending through the catheter wall which opens passively due to pressure (about 80 mm Hg) and vacuum (−7 mm Hg, though practically it often takes much more vacuum).

Russian patent 2,514,536 C1 discloses a method for formation of a subclavian-shoulder fistula. The '536 teaches forming an end-to-side venous anastomosis of a catheter with a subclavian vein on a border with an axillary vein. The catheter is placed on the front surface of the shoulder as a "suitcase handle" in a subcutaneous tunnel maximum rectilinearly in the optimum position for further puncturing in the deltoid region. The '536 teaches it utilizes more extended portion of the catheter for the puncture in contrast to the closest analogue. The '536 does not disclose details about the catheter. The '536 teaches a method that enables creating favourable conditions for fistula outflow ensured by low hydrostatic pressure in accessible veins of an upper limb. '536 does not disclose a two-way valve built into the very tip of the catheter.

Russian patent 2,556,787 C2 discloses a method for creating arteriovenous fistula in patients with used vascular age. The '787 teaches creating an arteriovenous fistula between the common iliac artery and the common iliac vein by delivering a prosthesis in subcutaneous fat of the anterior abdominal wall and creating a loop-shaped tunnel. The '787 does not disclose details about the catheter, and it does not disclose a two-way valve built into the tip of the catheter.

Non-patent literature titled "Vascular access for chronic dialysis using the superficial femoral vein", by Kapala et al., in *The Journal of Vascular Access* 4.4 150-153 (2003), discloses a method to create hemodialysis arteriovenous fistulas. The femoral vein is harvested and transplanted in the arm between the brachial artery and axillar vein, followed by an end-to-side anastomosis. In two patients, the venous graft remained on the anterior surface of the thigh. In those patients, they were extended with either a piece of polytetrafluoroethylene (PTFE) graft or the saphenous vein. The method disclosed by Kapala et al. does not utilize a catheter with a two-way valve in the tip.

There is a need in the art for a vascular access device that permits continuous access to the circulation with minimal inflammation. There is also a need in the art for a venous vascular access device allowing reliable removal and return of 250 to 400 mL/min blood flow without complications. There is need in the art for vascular access devices with flow that does not disturb the vascular epithelium.

SUMMARY

This proposal describes an approach to vascular access, one that more closely matches nature's design of vascular connections in the body, and the natural connections of streams and rivers. In one aspect of the invention, the present application teaches a two-way valve built into the very tip of the tributary access device (TAD). The present application is different than either the '263 or the '879 in that the two-way valve is built into the very tip of the TAD. Flow is out the longitudinal tip of the TAD and not the sides. The two-way valve will act passively, but it should have low opening and closing pressures.

In one aspect of the invention, a new type of TAD is disclosed for infusing fluid into veins and withdrawing blood from them. The Tributary Venous Access (TVA) includes a catheter which is placed through a tributary vein near its connection to a larger "target" vein (see FIG. 1). During placement, the TVA is advanced so that its tip barely enters the target vein. After the catheter is placed and left in position, the tributary vein develops irritation and fibrosis and the contracts around the TVA, fixing it in position. The subcutaneous portion of the TVA is tunneled under the skin to an exit site a small distance from the vein entry site.

A polyester cuff on the subcutaneous portion creates inflammation fibrous ingrowth into the cuff from the subcutaneous tissue, fixing the TVA in position and preventing bacteria from passage around the TVA. For larger size TVA devices such as those used for hemodialysis, a two-way valve can be built into the tip of the TVA. This serves as a diffusion barrier, to keep blood out of the TVA and lock solution within the TVA, between uses. Obviously, the valve must allow flow in either direction, with minimal pressure drop. It must also be smooth on both sides to prevent coagulation of blood. A "flap" valve fits these requirements. The valve does not have to seal perfectly to limit diffusion of blood or fluid around it.

In the TAD the goal is to withdraw blood through a port built into the side of a native vein, and return blood through a similar port in a somewhat distant native vein. When used for removal of blood, the ideal target vein for location of these ports is one that has high flow and always a positive pressure. If the target vein is always under positive pressure, then nearly all of the blood flowing through the vein can be removed through the side-port without causing collapse of the vein.

One way to position the side-port access in the target vein is to place a thin-walled catheter into a tributary vein, and then advance the catheter to a position so that tip barely reaches inside the wall of the target vein. If the catheter is roughly the same size as the tributary vein, then the vein will tend to constrict around the catheter. This fixes the position of the catheter relative to the target vein and prevents outward or inward movement. The tributary vein naturally flexes in synchrony with the target vein, as the limbs or extremities move, and this helps to position the catheter so that it moves with both veins. Of course, placement of the catheter in the tributary vein, and subsequent constriction of the vein around the catheter will obstruct flow through the tributary vein. Fortunately, the venous system is quite redundant in humans, and collateral veins exist to carry blood whenever one peripheral vein is lost or obstructed. Blood that was carried in the tributary vein will automatically find its way through the collateral veins. Edema of a limb occurs only when the major vein draining the limb, or a more central vein is obstructed.

The TAD is envisioned to be used intermittently, for blood removal and return to the body. When blood is flowing through the outflow and inflow catheters, there is little chance for the blood to clot within the catheters. In between use of the access, it would be filled with an anticoagulant lock solution, as are the current CVCDs. However, any catheter filled with stationary lock solution and placed in contact with flowing blood will tend to fill with blood at the tip, for several reasons. CVCDs often have side-holes and tiny pressure gradients which cause blood to flow through the side-holes and out of the tip, rinsing out the lock solution. The density of the lock solution is never exactly the same as blood, and therefore depending upon the position of the patient, gravity causes blood and lock solution to exchange positions. Finally, some blood diffuses from the blood stream into the catheter lumen. As blood enters the catheter the lock solution is diluted, and eventually the blood can clot within the tip of the catheter. These clots can sometimes be removed easily by flushing the catheter with sterile saline, but sometimes removal of the clot is more difficult.

To prevent clotting within the TAD between uses, we propose an additional element. This is a smooth-surfaced bidirectional valve that covers the tip of the catheter. This valve will passively open when blood is removed from the vein and when it is returned to the vein. As opposed to U.S. Pat. No. 5,290,263 by Wigness and U.S. Pat. No. 4,549,879 by Groshong, the valve of the TAD will be on the tip, rather than on the sides of the end of the catheter. The opening pressure of the valve will be lower than that for these previous designs also. When the catheters are filled with antithrombotic lock solution, the solution will not be diluted by blood entering the catheter. Since the valve will have a small slit between neighboring portions, so at a very slow rate some of the lock solution will also egress through the slit and coat the outside of the valve. Also, since the valves will be created from very thin materials (such as 0.005" thick) some of the lock solution can actually diffuse through the valve surfaces. With the bidirectional valve in place, the catheter should not develop internal clots between uses. Clots that might form on the blood side of the valve should be easily dislodged by passage of fluid or blood with the next use. A further benefit of the valve is that it will have an opening pressure slightly above the pressure of the target vessel. The outside portion of each tube of the TAD will have a Luer-Lock connector to connect to tubing of infusion devices or blood treatment devices. Between uses the catheter will be filled with lock solution and the connector will be capped. If perchance the cap comes loose, blood will be prevented from egress through the catheter and connector. Likewise, air will be precluded from entering the catheter and connector. In CVCDs and in peritoneal dialysis catheters, extension tubing and clamps exist between the catheter lumens and the connectors, to prevent blood loss or air inlet to the catheter if the cap should fall off the connector. With the TAD the valve serves this back-up protection role. This means that the tubing of the TAD outside of the body can be very short. The tubing will be durable enough to be able to be clamped during times of manipulation of the catheter or connection other tubings, as a further prevention of unintended flow.

In one aspect of the invention, a TAD is disclosed comprising a catheter with a valve on the tip. The catheter is connected to a tributary vessel adjacent to a target vessel in an end-to-side connection. The valve has an opening pressure slightly above the pressure of the target vessel.

In a further aspect of the invention, the end-to-side connection is a port or an anastomosis.

In additional aspects of the invention, the valve is composed of very thin materials, and may be 0.0035" to 0.0065" thick. In further embodiment, the preferred thickness is 0.005".

In additional aspects of the invention, the valve is bi-directional.

In additional aspects of the invention, the bi-directional valve maintains full concentration of a lock solution within the catheter.

In additional aspects of the invention, the catheter is placed by "over the wire" techniques common in interventional specialties.

In further aspect of the invention, a mechanical connector is used to attach the catheter to the tributary vessel.

In additional embodiments of the invention, an expandable stent is used to reinforce the junction of the tributary vessel to the target vessel. The sent may be self-expanding or balloon-expandable. The stent may be covered in smooth plastic or metal.

In additional embodiments, the device of the invention is used in a method to access the vasculature. The method may position the catheter with the tip barely extending from the wall of the target vessel.

In further embodiments of the method, the target vessel has low or negative pressure, and the rate of blood removal is low enough so that the vein does not collapse.

In one aspect of the invention, a new type of TAD is disclosed for infusing fluid into arteries and withdrawing blood from them. The Tributary Arterial Access (TAA) includes a catheter which is placed through a tributary artery near its connection to a larger "target" artery.

In further embodiments of the method, the device is placed in an artery for blood removal.

In further embodiments of the method, the device is placed in a vein for fluid delivery.

In further embodiments of the method, the catheter is placed in an artery or vein with a high flow rate and continued positive pressure.

In an additional embodiment, a pair of TADs are used in a method for continuous-flow therapy. Blood is removed from a first vein via a first device at a first location, and blood is returned via a second device to a second location. The second location may be on a second vein or on the first vein at a distance from the first location.

In an alternative embodiment, a pair of TADs are used in a method for continuous-flow therapy. Blood is removed from a first artery via a first device at a first location, and blood is returned via a second device to a second location. The second location may be on a second artery or on the first artery at a distance from the first location.

In alternative embodiment of the continuous-flow therapy, a pair of TADs are used such that the first is connected to an artery and the second is connected to a vein. In other alternative embodiment of the continuous-flow therapy, a pair of TADs are used such that the first is connected to a vein and the second is connected to an artery.

BRIEF DESCRIPTION OF THE DRAWINGS

The above-mentioned and other features of this disclosure, and the manner of attaining them, will become more apparent and the disclosure itself will be better understood by reference to the following description of embodiments of the disclosure taken in conjunction with the accompanying drawings, wherein:

FIG. 4A1: Perspective view of the InterGraft system for minimally-invasive placement of an AV Graft using arterial connectors.

FIG. 4A2: Cross-section view of the InterGraft system for minimally-invasive placement of an AV Graft using arterial connectors.

FIG. 4A3: Perspective view of the InterGraft system for minimally-invasive placement of an AV Graft using venous connectors.

FIG. 4A4: Cross-section view of the InterGraft system for minimally-invasive placement of an AV Graft using venous connectors.

FIG. 5: Diagram of TAD created using a catheter with a balloon-expandable stent on the end closest to the target vein.

Figure 1:
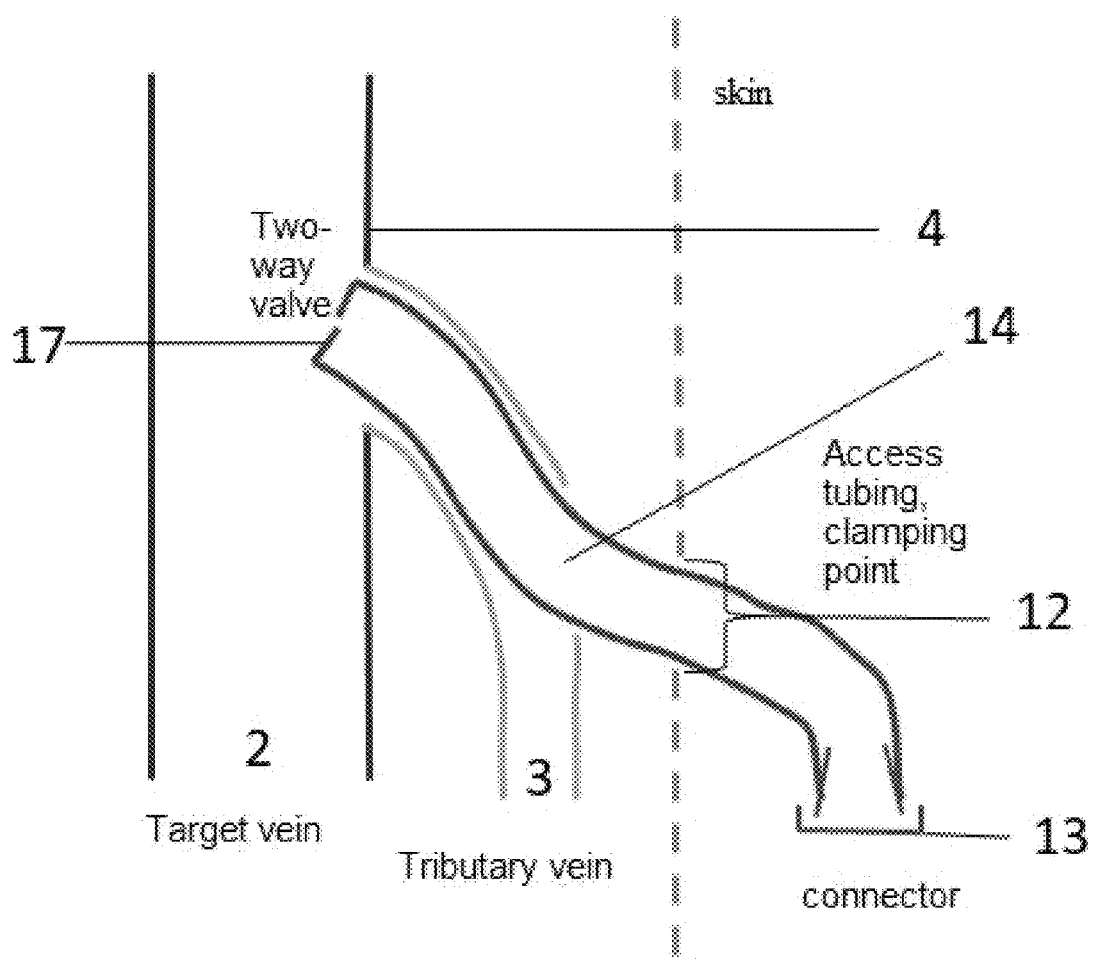
FIG. 1: Diagram of the main components of the TAD placed into a target vein through a tributary vein. For blood sampling or fluid infusion, only one Access Device is needed. For extracorporeal blood therapy requiring continuous blood flow, a second device is placed into another target vein.

Corresponding reference characters indicate corresponding parts throughout the several views. Although the drawings represent embodiments of the present disclosure, the drawings are not necessarily to scale and certain features may be exaggerated in order to better illustrate and explain the present disclosure.

DETAILED DESCRIPTION OF THE EXEMPLARY EMBODIMENTS

The embodiments disclosed below are not intended to be exhaustive or limit the disclosure to the precise forms disclosed in the following detailed description. Rather, the embodiments are chosen and described so that others skilled in the art may utilize their teachings.

Disclosed herein is a TAD device and method to access the vasculature. The device and method are introduced in a drawing of the TAD and its placement within a tributary and target vein in FIG. 1. The TAD 1 is comprised of a single lumen cylindrical catheter 14 with a two way valve in tip 17 for the internal end, and a connector 13 on the external end. The method comprises passing the TAD 1 through the skin 12 and into a tributary vein 3, then passing the TAD 1 along the tributary vein 3 towards a nearby junction with the target vein 2, and the positioning the TAD 1 so that tip 17 extends a few millimeters past the wall of the target vein 4.

For purposes of hemodialysis, where blood flow rates of 300 ml/min or more are desired, it is necessary to have a target vein that carries a large amount of blood and also always has positive pressure. The femoral vein fits this need fairly well, with blood flow rates of 250-400 ml/min (depending on body size). In one embodiment of the invention, the common femoral vein in the human is the best candidate for implantation of the TAD. The femoral vein has sufficient rate of blood flow, and flow increases markedly with exercise. Due to the effects of gravity and pressure on the inferior vena cava by the liver and abdominal contents, the femoral vein has a positive pressure in patients regardless of whether the patient is standing or supine. Only when the patient is severely hypovolemic does the pressure decrease towards zero.

Figure 2A:
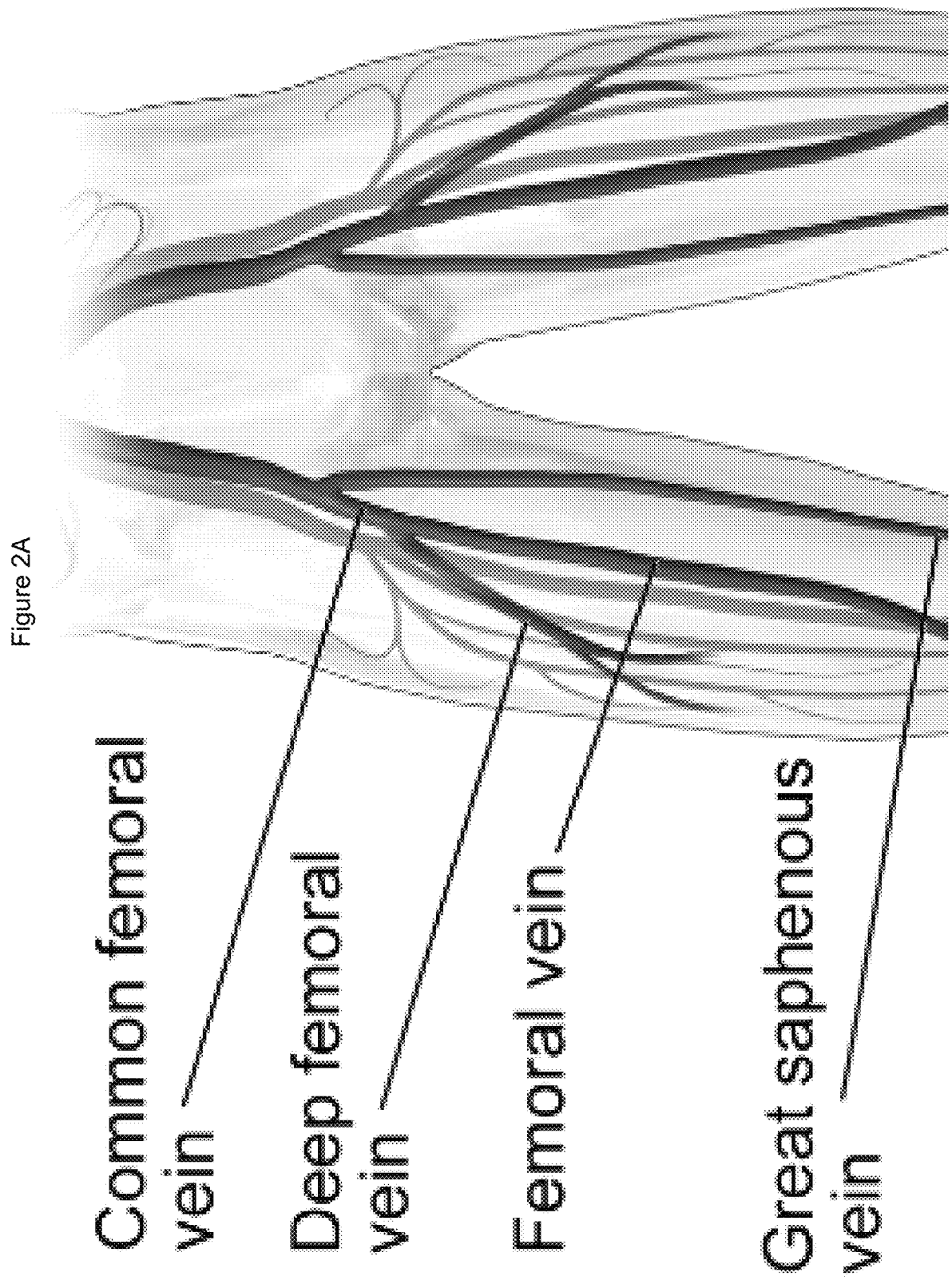
FIG. 2A: Diagram of the junction of the saphenous vein to the common femoral vein.
Figure 2B:
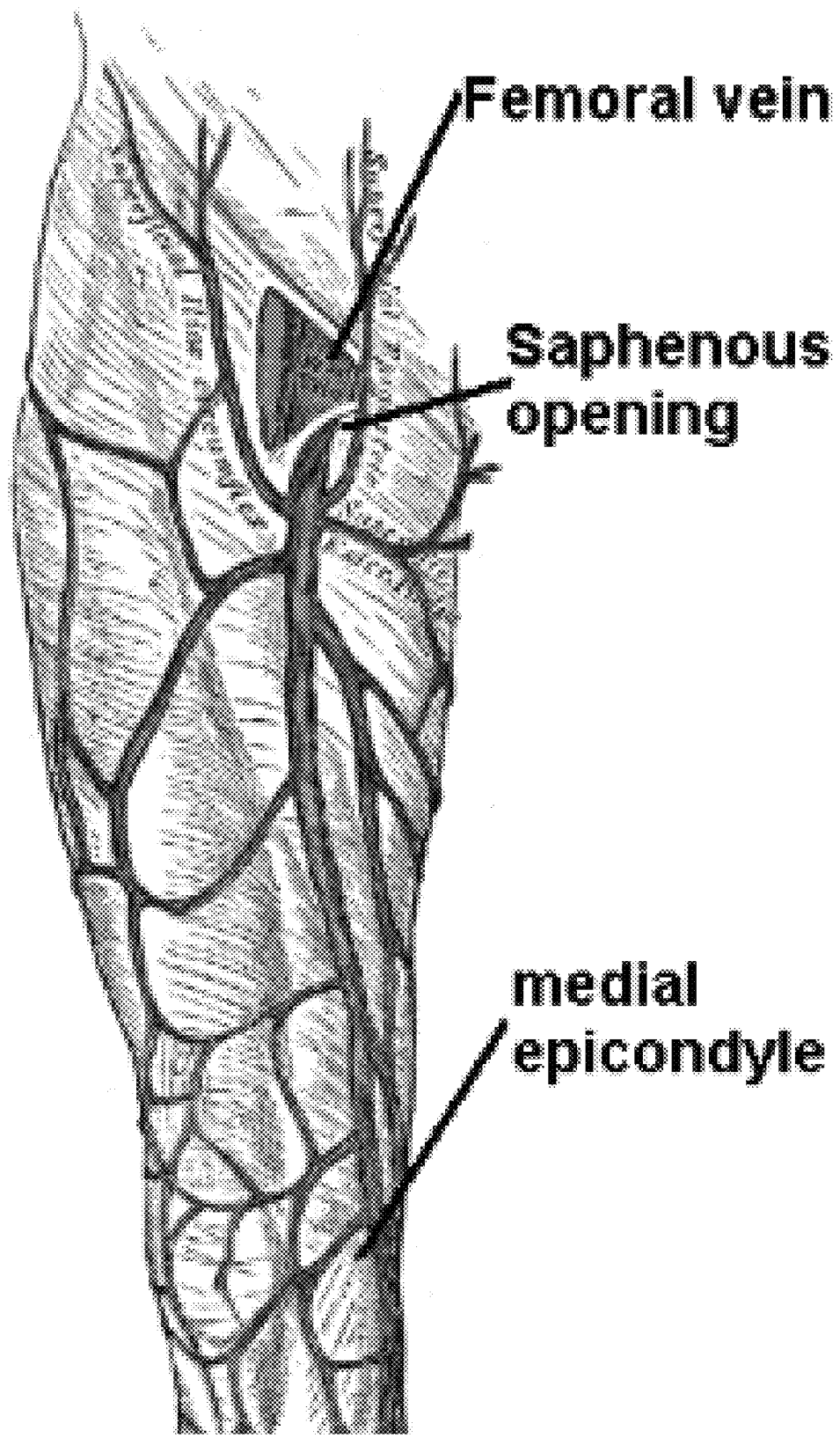
FIG. 2B: View showing numerous subcutaneous collateral veins of the saphenous vein.

As best illustrated in FIGS. 2A and 2B, the femoral vein near the inguinal ligament has a relatively fixed position due to effects of the femoral sheath and the fascia around the leg muscles. Also, the femoral vein has a large tributary vein in the greater saphenous vein, which has a junction to the femoral vein near the inguinal ligament, where it passes through a large foramen in the fascia surrounding the muscles of the leg. The saphenous vein may be removed or obstructed without causing leg edema in most patients. This is because there are numerous collateral veins in the leg, connecting the other veins in the body. The saphenous vein is frequently removed to provide veins for coronary artery bypass grafts (CABG procedures). The saphenous vein is also coagulated and obliterated as a therapy for varicose veins, which develop when valves in the saphenous vein become incompetent. The size of the average saphenous vein is 5+/−2.4 mm. Thus, it would easily allow a 3 to 5 mm diameter catheter to be inserted through the upper portion of the vein to reach the femoral vein junction. While the saphenous vein has numerous valves, the common femoral vein usually has either one or none between the saphenous vein junction and the external iliac vein. Finally, the saphenous vein is quite superficial and close to the skin surface, even in patients with moderate obesity.

In additional embodiments of the invention, for purposes of fluid infusion and blood sampling, a small diameter TAD could be placed into just about any vein in the body that connects to a larger vein. To utilize veins with the highest blood flow rate however, those of the inguinal area or lower neck are preferred.

Figure 3:
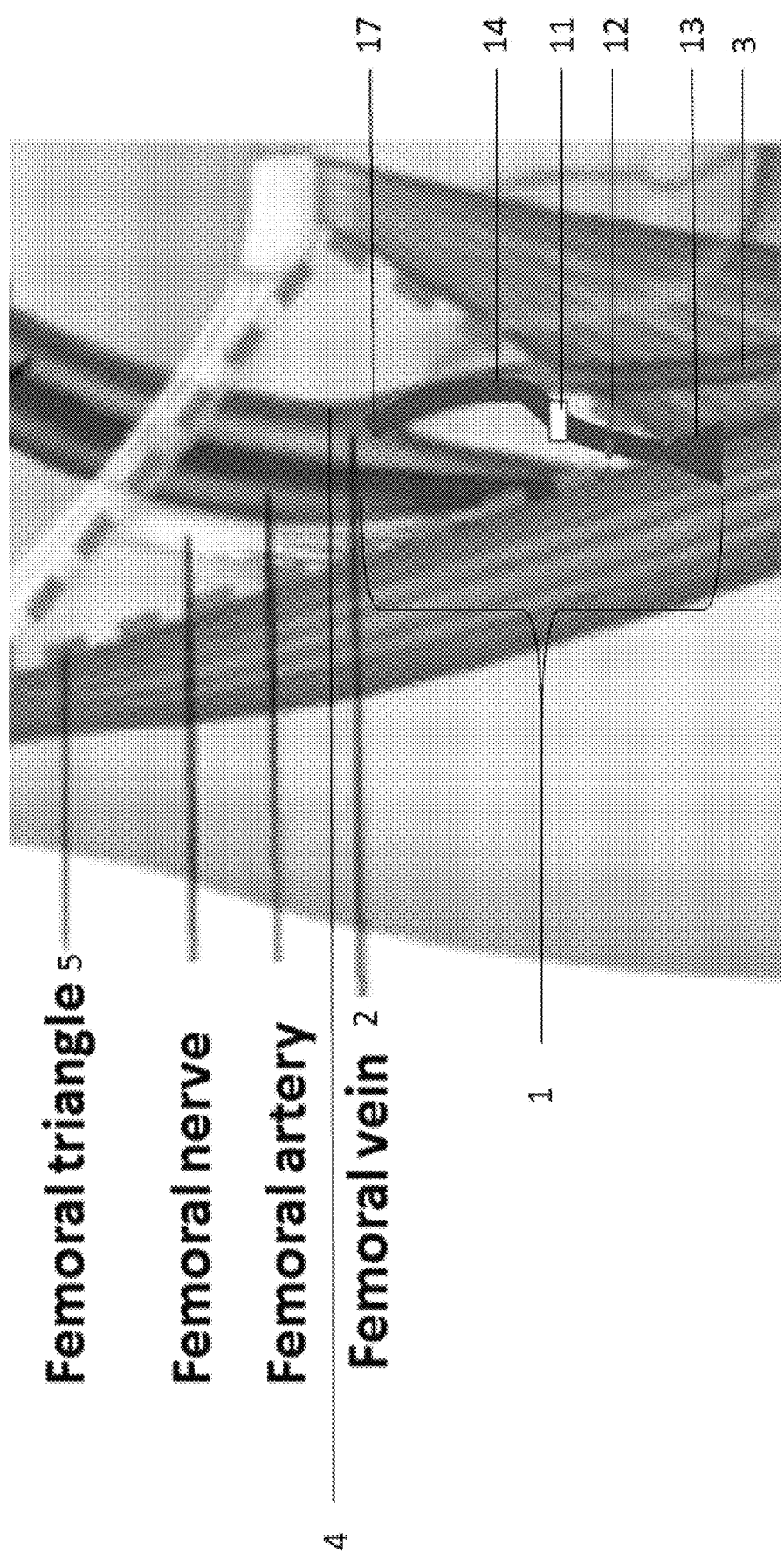
FIG. 3: Diagram of the TAD placed through the saphenous vein to reach the common femoral vein and extend a slight distance past the wall of the target vein. Position of the subcutaneous cuff is shown by the white rectangle. Dotted line is at the skin exit. Triangle indicates external connector.

The components of an exemplary embodiment of TAD 1 and the method of use attaching it to a femoral vein 2 are shown in FIG. 3. The single lumen cylindrical catheter 14 courses through the skin, enters the greater saphenous vein 3, passes through the junction of the saphenous and femoral veins and extends into the femoral vein a few millimeters, the two-way valve is pre-formed on the tip 17 of the TAD.

In additional embodiments, the single lumen cylindrical catheter 14 extends into the femoral vein 1 to 3 millimeters.

In the exemplary embodiment, the subcutaneous tract of the TAD includes a subcutaneous cuff to promote ingrowth of fibrous tissue, similar to a peritoneal dialysis catheter and a chronic CVCD. This fibrous plug serves to fix the catheter in position and to passage of bacteria around the catheter, past the hub, and towards the tributary and target veins.

As illustrated in FIG. 3, the pre-attached Dacron cuff 11 is positioned in the subcutaneous tissue between the exit site and the saphenous vein entry point. The external connector 13 is also pre-attached or molded to the catheter 14, and rests about one inch from the skin exit site 12.

In an alternative embodiment, the TAD 1 as described above can be placed through the skin using Seldinger transcutaneous techniques, in a manner similar to placement of a chronic tunneled CVCD. An ultrasound could be used to locate the saphenous vein 3 near the femoral triangle 5. A small incision 12 would be made in the skin, near to the desired point of entry to the saphenous vein 3. A needle could be placed through this incision 12 and directed at a low angle to reach and penetrate the saphenous vein 3. A guidewire could be placed through the needle and advanced through the saphenous vein 3 into the femoral vein 2, and then into the external iliac vein. Another small skin incision could be made an inch or two caudal (footward) from the original incision, and a tunnelor device could be used to pull the tip of the TAD from the first incision through subcutaneous fat layer and then out of second incision. The subcutaneous cuff 11 could be positioned under the skin at a location so that the tip of the TAD will just reach the femoral vein wall 4. A dilator and surrounding split-sheath will then be advanced over the guidewire and into the femoral vein. The guidewire and dilator could be removed so that the split-sheath remains (a valve on the outer end of the sheath prevents bleeding at this point). The tip of the TAD is then passed into the split-sheath and towards the femoral vein. The split-sheath is removed when the Access is fully inserted. Using fluoroscopy and if with injection of small amounts of x-ray contrast, the catheter will be adjusted slightly back and forth to assure that the tip passes into the femoral vein by only 1-3 mm. Attaching a syringe to the outer connector, blood will be withdrawn from the access and saline will be injected, demonstrating adequate function. The primary skin incision will be closed using subcutaneous absorbable sutures.

This design results in only a small amount of foreign material residing in the vein which should diminish systemic inflammation (3). Avoiding catheter contact within the walls of central veins should diminish irritation of the vein wall and minimize development of fibrous sheathing and central venous stenosis that almost always occur with CVCD. The valve should prevent blood from entering the tributary catheter when it is locked and capped after treatments, and will also maintain a high concentration of an antibacterial and antiseptic catheter lock solution within the catheter portion between treatments. If there is contamination of the hub and internal lumen of the catheter during access, the lock solution can directly contact the entire inner surface of the catheter and help to eliminate bacteria and biofilm. When such catheter locks are used in CVCD they contact the inside of the catheter temporarily, but the lock is quickly diluted by blood at the tip of the catheter. Also, the outside of a CVCD catheter is usually contaminated when the lumen is contaminated. In the TAD the outside of the catheter will not contact flowing blood in the femoral vein, except for the tiny portion resting in the vein.

In another embodiment, another way to create a TAD is to create an artificial connection between a subcutaneous catheter and a large vein. Creation of a workable suture-less end-to-side anastomosis has been the goal of many physicians and companies. BioConnect Systems (Ambler, Pa.) has been the most successful. The Optiflow™ device by BioConnect has a short entry tube (conduit) to connect to an artery and a flange that expands to seal against the inner surface. Optiflow devices have been used to create fistulas in 41 patients with ESRD, with an unassisted primary patency rate of 78% at 90 days (7). A limitation of this technology is that the creation of the anastomosis is still essentially a surgical procedure, though performed without sutures at the anastomosis to the artery.

Figure 4B:
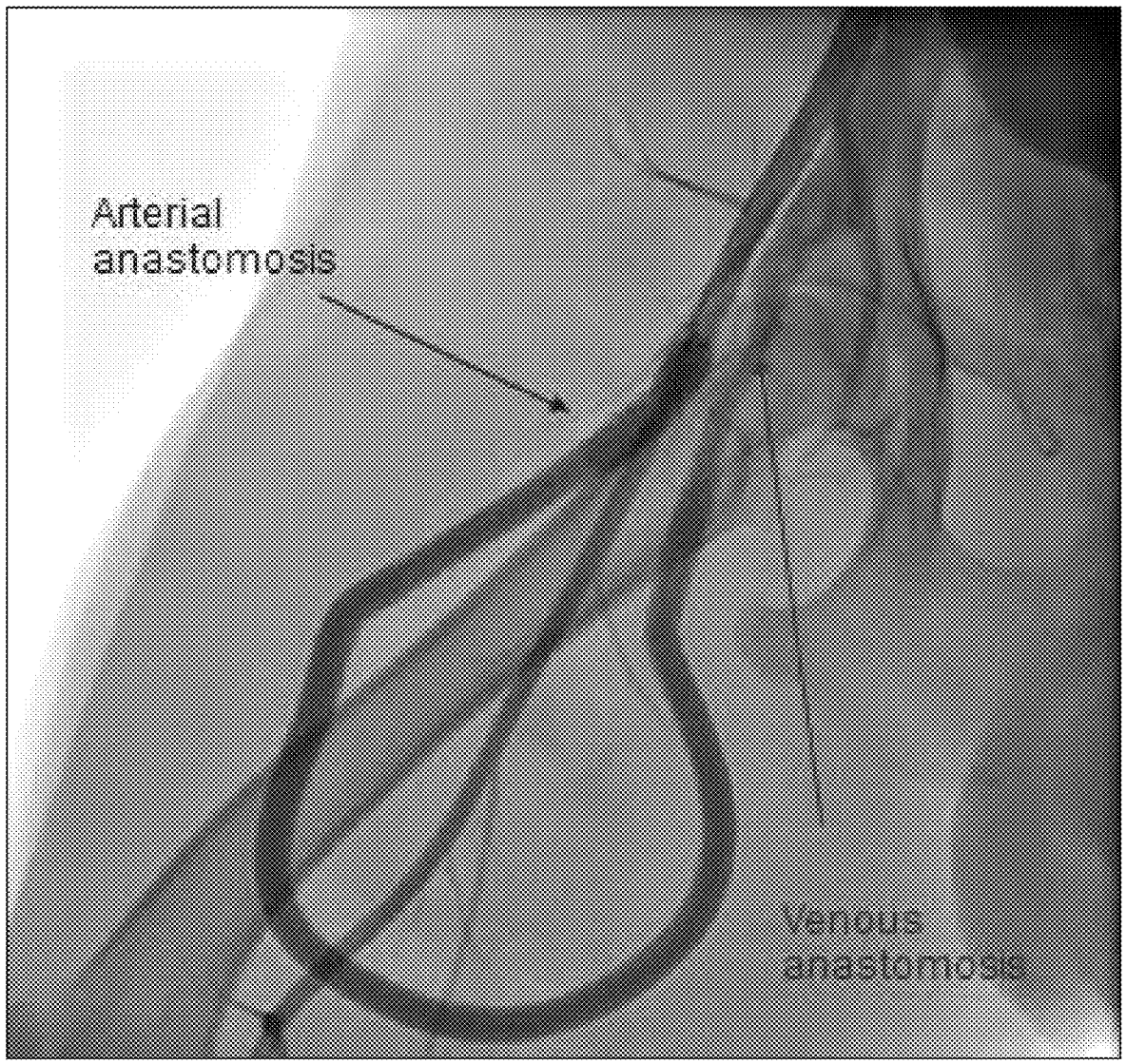
FIG. 4B: InterGraft system for minimally-invasive placement of an AV Graft, Angiogram at 3.5 hrs. post-implantation in a dog model.

Recently a new approach to creating a suture-less end-to-side anastomosis has been developed by Dr. Yevzlin and Phraxis, Inc., as part of the InterGraft™ system (8). The InterGraft is a subcutaneous AV graft that can be placed using small incisions and minimally invasive over-the-wire techniques for connection to both the artery and vein. The arterial connector shown in FIGS. 4A1 and 4A2 is a covered stent-like device that is deployed into the artery in collapsed form over an 0.014" guidewire, and then expanded, opening tines that engage the intima of the artery as the connector is pulled back. A flexible section of the connector attaches to a six mm ID PTFE graft that is pulled under the skin, and a straight covered stent-like device attaches the venous limb of the graft to the native vein. Long-term animal studies of the InterGraft have demonstrated patency of the grafts and absence of stenosis at the anastomosis, and a clinical trial has demonstrated successful anastomosis placement in patients with arteries free of significant disease. The InterGraft connector is designed to be used for connection to arteries, but with some minor modifications could be used to connect to veins (see FIGS. 4A3 and 4A4). As illustrated in FIG. 4B, it could then be used to create a TAD, connecting a catheter in an end-to-side anastomosis to the venous system. Some extra technology would have to be applied to install a two-directional valve at the opening to the vein.

Another embodiment is illustrated in FIG. 5, it shows a third way to create a TAD 1 using stent technology. The tip of the catheter could be created by a stent 15, which is a thin metal screen which is expandable to fit the shape of a surrounding vein. After a stent 15 is placed, the metal elements are covered by some of the intimal lining of the blood vessel, so they fuse together. Eventually the stent 15 becomes completely covered with the intimal cellular material, and the surface may have the appearance of the surrounding native vessel. The stent 15 would be placed into the portion of the tributary vein 3 closest to the target vein 2, so that this portion would not collapse under negative pressure or expand under positive pressure. The stent 15 could be bare metal or could have an internal lining of porous plastic material such as expanded PTFE (a "covered" stent). Either type would form a naturally-shaped entry to the large vein, for the Tributary Vein 2. A bidirectional valve 16 could be constructed as part of the stent 15 or placed in a separate procedure (like a miniature heart valve replacement, placed by endovascular techniques).

Tip 17 is at the internal end of single lumen cylindrical catheter 14. The bi-directional valve 16 is comprised of flap 18 and hinge 19. Flap 18 is attached to hinge 19, and hinge 19 is attached to the inside of tip 17.

Figure 6A:
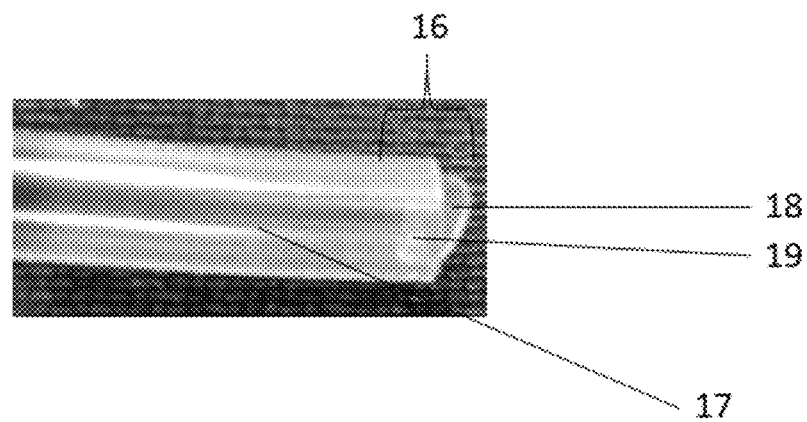
FIG. 6A: Illustration of TAD in the open or flap out position.
Figure 6B:
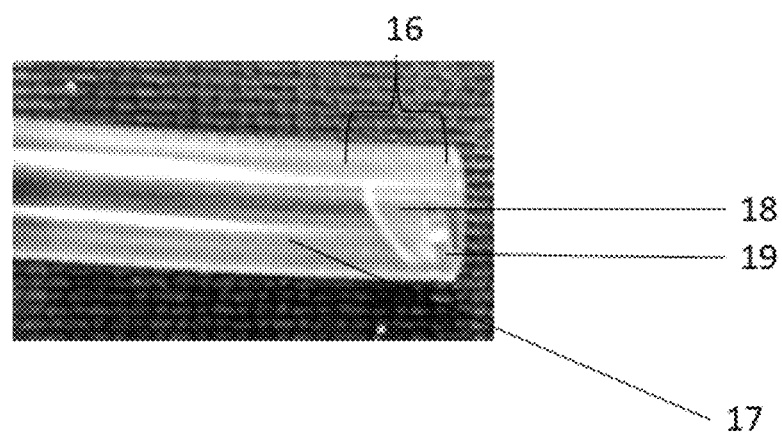
FIG. 6B: Illustration of TAD in the closed or flap in position.

A flap design is used for the bi-directional valve 16 in the tip of the TAD 17. FIG. 6A displays a TAD that is open or in the flap out position. FIG. 6B displays a TAD that is closed or in the flap in position.

Figure 7A:
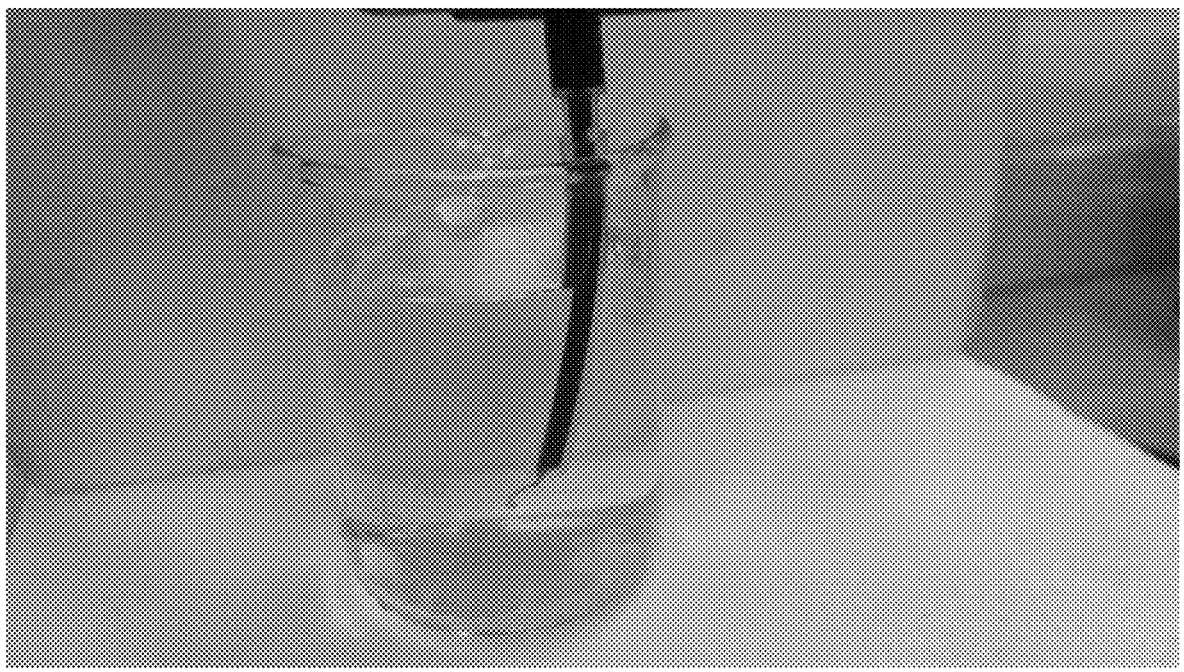
FIG. 7A: Illustration of TAD filled with colored lock solution in the closed position.

A TAD is filled with colored solution to test the seal of the flap design. As illustrated in FIG. 7A, when the TAD is in the perpendicular position, gravity causes water and the colored solution to exchange positions to a small degree.

Figure 7B:
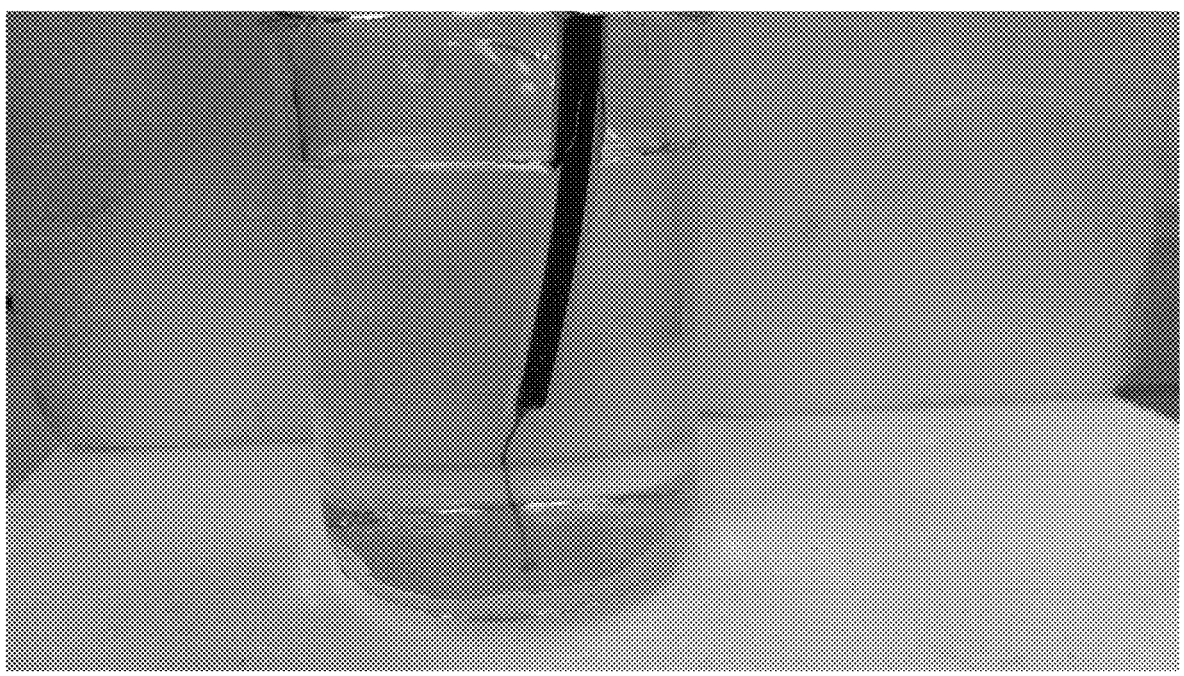
FIG. 7B: Illustration of TAD filled with colored lock solution in the open position.

As illustrated in FIG. 7B, the flap design results in a valve that opens when the pressure inside the catheter exceeds the external pressure. In this example, hydrostatic pressure is exerted by the height of colored solution in the TAD above the level of the external solution in the beaker. The hydrostatic pressure causes the bi-directional valve in the tip of the TAD to open.

The TAD described above is a simple Luer-Lock with a cap, and the skin exit site is a small skin penetration carrying a single lumen tube. The catheter is held in position by fibrous ingrowth into the subcutaneous porous cuff (such as Dacron® felt). The subcutaneous portion of the catheter and the exit site are very similar to a peritoneal dialysis catheter, except that the external tubing would be much shorter. There would be two exit sites of the TAD pair, each in the upper and inner portion of the front of the thigh. One Access would be used for blood removal and the other for blood return, so that the blood withdrawn is from that passing from the leg and the blood is returned to the opposite leg. The use of a TAD in separate veins assures that there will not be recirculation of blood from one Access to the other. Alternatively, both Access devices could be placed on the same vein, with blood being withdrawn "upstream" from the vessel, and blood being returned is put "upstream".

Alternating the direction of flow in the Access pair from one treatment to another might help to assure that clots do not form over the surface of one of the connectors. Or, if one Access provides better outflow of blood, this one could always be used for blood removal. Alternatively, some dialysis machines are designed to use only one blood access point. These machines draw blood out, then pause briefly, and return an equal amount of blood that has passed through a dialyzer. For these "single access" machines, only one TAD would be needed.

There are a number of variations that could be made for the skin exit sites, using known technology: The first variation is that the external connector could be built into a skin-level device that includes a Luer-Lock for tubing connection, surrounded and fixed by Dacron felt. The safety valve for access could be built into the connector apparatus. The second variation is a subcutaneous port could be provided for each Access device, which would be entered by needle puncture of the skin (similar to the Dialock® device, no longer available). A third variation is a double-lumen tube could be connected to each of the TADs, to carry blood flow to and from the Access devices through a single skin exit point (such as on the lower abdomen).

Combined with an antiseptic-antithrombotic catheter lock solution and a suitable valve to maintain a lock solution within the tubing between uses of the catheter, the TAD could: Provide immediate use and painless blood access, similar to a CVCD; Reduce complications of sheathing, inconsistent blood flow, central vein stenosis, systemic inflammation and infection associated with CVCD; Avoid many problems of AV fistulas and grafts including: delay in use, failure to mature, pain of repeated needle-sticks, bleeding after dialysis, venous and anastomotic stenosis, central vein stenosis, aneurysms, pseudo-aneurysms, arterial steal syndrome, arterial emboli, and frequent interventions; Provide a single exit site in the lower abdomen or two access points in the upper thighs, avoiding disfigurement of the limbs and upper chest caused by today's vascular access approaches, and creating convenient access points for wearable dialysis devices; Permit placement by percutaneous interventional techniques, under local anesthesia with minimal sedation, and without need for dissection and occlusion of blood flow within the vein.

This project includes three innovations in the field of dialysis vascular access. The first innovation is the use of a large peripheral vein for obtaining blood flow for dialysis by using an end-to-side port rather than by a catheter lying within a central vein or a needle inserted into an AV graft or AV fistula. The second innovation is an end-to-side anastomosis between a native vein and a plastic conduit using a port employed by over-the-wire techniques. With interventional techniques, a needle enters directly into a vein that is not surgically isolated while blood is flowing in the vein, as opposed to surgical techniques that involve dissection of adventitia, closure of collateral veins, obstruction of venous flow and a venotomy by scalpel. This end-to-side venous anastomosis may be valuable in other areas of vascular therapy, such as in shunting blood around venous obstructions or occlusions. The third innovations is a valve within the end-to-side anastomosis to close the port between uses and yet allow injection of saline and catheter lock solution to clear blood from the access tubing while the valve is closed. By preventing blood entry to the tubing between dialysis treatments the valve will prevent dilution of the lock solution and thus prevent clotting within the access tubing. An antiseptic and anticoagulant lock solution such as Zuragen™ will maintain full concentration and effectiveness in prevention of clotting and removing biofilm and associated organisms from all exposed surfaces. The valve mechanism on the venous port also obviates the need for external extension tubing and clamps, as are used with current CVCD. A valve such as this would be of considerable value to close the tip of current central venous catheters for dialysis. The valve described above is passively opened by the pressure of fluid or blood flowing through the valve. It is also possible to create a valve that is actively opened or closed by operation of a mechanical or electronic switch outside the body.

If successful, the TAD will be the first new approach to dialysis vascular access since 1990. It would then form a valuable "fourth option" for dialysis vascular access. The same TAD could also be valuable in providing high blood flow rates for other extracorporeal therapies, such as plasmapheresis, oxygenation and decarbonation of blood (for treatment of respiratory insufficiency), sorbent treatment of blood (for various conditions) or bio-artificial devices for endocrine therapy. A smaller version of the TAD would be valuable for many applications of intermittent infusion therapy (such as in total parenteral nutrition) or blood removal for chemical sampling such as glucose monitoring in diabetics, physiological measurements in chronic diseases, or drug concentration measurement during chemotherapy. For many of these measurements and therapies the rate of blood removal is very small, and the TAD could be placed into veins that do not always have positive pressure but do have continuous flow (such as veins of the arm, neck or upper chest). Finally, while we have described the TAD as a device for removal from veins, it would obviously serve to remove blood effectively from arteries. With arterial access however, extreme care would have to be given to prevent accidental blood discharge, and complications of placement or use of the access would be more serious than with venous access.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

What is claimed is:

1. A method to access a vasculature comprising:
providing a tributary access device (TAD); wherein the TAD comprises a single-lumen catheter,
passing the single-lumen catheter through a skin of a user, then
passing the single-lumen catheter through a tributary vessel towards a nearby junction with a target vessel, and
positioning the single-lumen catheter so that a tip of the catheter extends no more than 1-3 millimeters within a wall of the target vessel,
wherein the catheter is connected to the target vessel in an end-to-side connection by neo-intimal sheathing or stenosis of the tributary vessel and without surgical anastomosis of the target vessel or the tributary vessel.

2. The method of claim 1, wherein the single-lumen catheter comprises a subcutaneous cuff, a bi-directional valve, and an external connector, wherein the bi-directional valve is in the tip of the catheter, wherein the subcutaneous cuff is on an opposite half of the catheter from the tip, and wherein the external connector is pre-attached or molded to a catheter end opposite from the tip.

3. The method of claim 2, wherein the catheter is placed by over the wire techniques common in interventional specialties.

4. The method of claim 2, wherein the target vessel has low or negative pressure, and the rate of blood removal is low enough so that the target vessel does not collapse.

5. The method of claim 2, wherein the tributary access device is placed in an artery for blood removal.

6. The method of claim 2, wherein the tributary access device is placed in a vein for fluid delivery.

7. The method of claim 6, wherein the catheter is placed in a femoral vein.

8. The method of claim 2, wherein the catheter is placed in an artery or vein with a high flow rate and continued positive pressure.

9. The method of claim 2, wherein the catheter is placed into a tributary vessel, further comprising a flexible connector pre-attached or molded to the catheter to attach the catheter to the tributary vessel.

10. The method of claim 1 wherein the catheter is directed to enter a tributary vessel, and advanced through the tributary vessel so that the catheter tip extends into the target vessel.

11. A method for continuous-flow extracorporeal therapies comprising:

providing a first tributary access device (first TAD) and a second tributary access device (second TAD), each comprising a single-lumen catheter, connecting the first TAD single-lumen catheter to a first location and the second TAD single-lumen catheter to a second location through a method to access a vasculature comprising:

passing each single-lumen catheter through a skin of a user, then passing each single-lumen catheter towards a nearby junction with a target vessel, and positioning each catheter so that a tip extends no more than 1-3 millimeters within a wall of the target vessel, wherein each single-lumen catheter is connected to the target vessel in an end-to-side connection by neo-intimal sheathing or stenosis and without surgical anastomosis, removing blood from a first vessel via the first TAD single-lumen catheter at the first location, and returning blood to a second vessel via the second TAD single-lumen catheter at the second location, wherein the first and the second vessels are selected from the group consisting of an artery and a vein.

12. The method of claim 11, wherein the first vessel, is a first vein and the second vessel is a second vein.

13. The method of claim 11, wherein the first vessel is a first vein and the second vessel is in the first vein at a distance from the first location.

14. The method of claim 11, wherein [the] each single-lumen catheter comprises a subcutaneous cuff, a bi-directional valve, and an external connector, wherein the bi-directional valve is in the tip of the catheter, wherein the subcutaneous cuff is on an opposite half of the catheter from the tip, and wherein the external connector is pre-attached or molded to a catheter end opposite from the tip.

\* \* \* \* \*